United States Patent
Rongione et al.

(10) Patent No.: US 6,284,901 B1
(45) Date of Patent: Sep. 4, 2001

(54) DINITRILE INTERMEDIATES FOR THE SYNTHESIS OF OMAPATRILAT AND METHODS FOR PRODUCING SAME

(75) Inventors: Joseph C. Rongione, Highlands, NJ (US); Robert G. Brown, Houston, TX (US); Dwight E. Raff, West Milford, NJ (US)

(73) Assignee: Dixie Chemical Company, Pasadena, TX (US)

( * ) Notice: Subject to any disclaimer, the term of this patent is extended or adjusted under 35 U.S.C. 154(b) by 0 days.

(21) Appl. No.: 09/589,582

(22) Filed: Jun. 7, 2000

Related U.S. Application Data

(60) Provisional application No. 60/172,335, filed on Dec. 17, 1999, and provisional application No. 60/172,440, filed on Dec. 17, 1999.

(51) Int. Cl.[7] ...................... C07C 255/04; C07C 253/14; C07D 317/00
(52) U.S. Cl. ........................... 549/448; 558/445; 558/346
(58) Field of Search .............................. 549/448; 558/445, 558/346

(56) References Cited

U.S. PATENT DOCUMENTS

| | | | | |
|---|---|---|---|---|
| 3,424,783 | * | 1/1969 | Harper et al. ...................... | 260/465.5 |
| 3,862,203 | * | 1/1975 | Greco et al. ....................... | 260/465.5 |
| 4,039,527 | * | 8/1977 | Nagaoka et al. ................... | 260/192 |
| 4,543,215 | * | 9/1985 | Brunnmuller et al. ........... | 260/465.5 |

FOREIGN PATENT DOCUMENTS

| | | |
|---|---|---|
| 14 93 752 A | 11/1969 | (DE) . |
| 806931 | 1/1959 | (GB) . |

OTHER PUBLICATIONS

Robl Et Al., "Dual Metalloprotease Inhibitors: Mercaptoacetyl–Based Fused Heterocyclic Dipeptide Mimotics as Inhibitors of Angiotensin–Converting Enzyme and Neutral Endopeptidase," *J. Med. Chem.*, 1997, 40, 1570–1577, Princeton, New Jersey.

Robl Et Al., "Dual Metalloprotease Inhibitors. 6. Incorporation of Bicyclic and Substituted Monocyclic Azepinones as Dipeptide Surrogates in Angiotensin–Converting Enzyme/Neutral Endopeptidase Inhibitors," *J. Med. Chem.*, 1996, 39. 494–502, Princeton, New Jersey.

Rousset, A., et al., "Systémes de strecker et Apparentés XI", vol. 36, 1980, pp. 2649–2661, XP002164112 p. 2651, left col. line 21—right col., line 17; p. 2651, eq. IV.VII.

Bejaud, M., et al., "No. 264.—Systémes de Strecker et Apparentés. VIII.", Bull. Chim. Soc. Fr., 1976, pp. 1425–1430, XP000985683.

Beilstein Informationssystme GmbH: XP002164119; BRN 1725961; & Snessarew; J. Pract. Chem., vol. 2, No. 89, 1914, p. 365.

\* cited by examiner

*Primary Examiner*—Floyd D. Higel
*Assistant Examiner*—Kamal Saeed
(74) *Attorney, Agent, or Firm*—Locke Liddell & Sapp LLP

(57) ABSTRACT

Omapatrilat (I) is a potent inhibitor of angiotensin-converting enzyme (ACE) and neutral endopeptidase (NEP) both in vitro and in vivo and is currently undergoing large scale clinical trials as an anti-hypertensive. Omapatrilat may be synthesized using the S-stereoisomer of a racemic mixture. The racemic mixture may be prepared from a hydantoin (III). The hydantoin may be prepared from a novel dinitrile compound (IV):

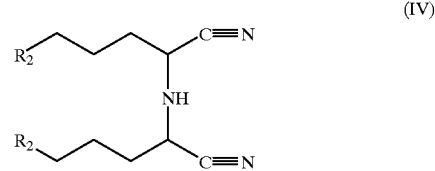

(IV)

The dinitrile may be produced by reacting a monoacetal with a non-carbonate ammonium salt and an alkali cyanide.

20 Claims, No Drawings

DINITRILE INTERMEDIATES FOR THE SYNTHESIS OF OMAPATRILAT AND METHODS FOR PRODUCING SAME

This application claims priority from U.S. Provisional Application Ser. No. 60/172,335 filed Dec. 17, 1999 and U.S. Provisional Application Ser. No. 60/172,440 filed Dec. 17, 1999, both of which are incorporated herein by reference.

BACKGROUND OF THE INVENTION

Omapatrilat (I) is a potent inhibitor of angiotensin-converting enzyme (ACE) and neutral endopeptidase (NEP) both in vitro and in vivo:

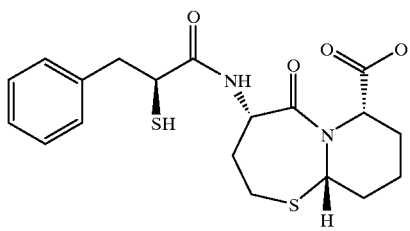
(I)

Omapatrilat was developed at the Bristol-Myers Squibb Pharmaceutical Research Institute as the first of a new class of compounds capable of simultaneously inhibiting ACE and NEP and is currently undergoing large scale clinical trials as an anti-hypertensive. See Omapatrilat. *Drugs R D* 1999 Apr;1(4):350–1.

Currently, omapatrilat is synthesized using (S)-hydroxy amino acid (II) as one of the key starting materials:

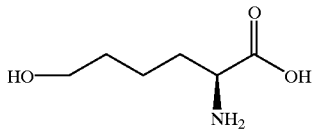
(II)

The hydroxyl group of compound (II) must be converted to an aldehyde as a prerequisite step in the synthesis os compound (I), omapatrilat. This oxidation to an aldehyde currently requires several steps and/or noxious reagents. See Robl, J. A., et al. *J. Med. Chem.* 1997, 40, 1570–1577; Robl, J. A., et al. *J. Med. Chem.* 1996, 39, 494–502.

It is therefore desirable to find alternatives to compound (II) that reduce the number of requisite synthetic steps and eliminate the use of noxious reagents. It is further desirable to develop a pathway suitable for the production of such intermediates.

SUMMARY OF THE INVENTION

The invention is directed to dinitrile intermediates of the formula:

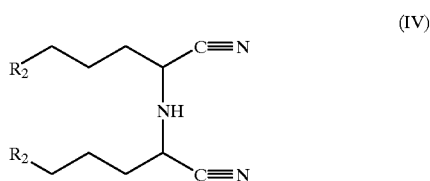
(IV)

wherein each $R_2$ is independently selected from:

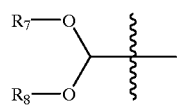
(VII)

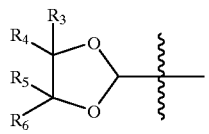
(VIII)

wherein $R_3$, $R_4$, $R_5$, and $R_6$ are independently selected from a group consisting of H or $C_1$–$C_5$ alkyl groups and $R_7$ and $R_8$ are independently selected from a group consisting of $C_1$–$C_5$ alkyl groups.

The compounds of the invention may be produced by the following schematic pathway:

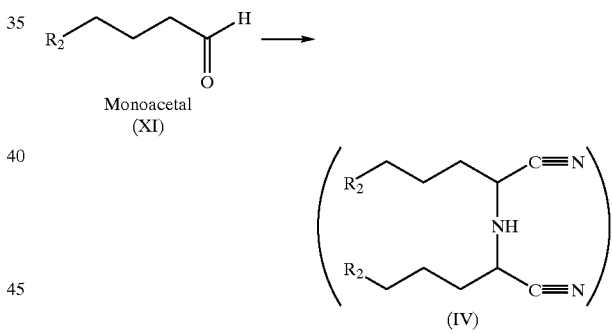

wherein $R_2$ is as defined above. This reaction is a step in the production of a racemic mixture of the formula:

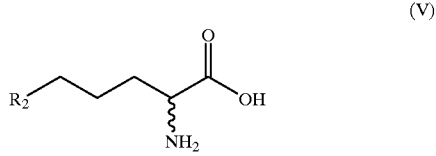
(V)

The racemic mixture of (V) may then be subjected to a separation process whereby the S-stereoisomer may be isolated. The overall reaction scheme may be summarized as follows:

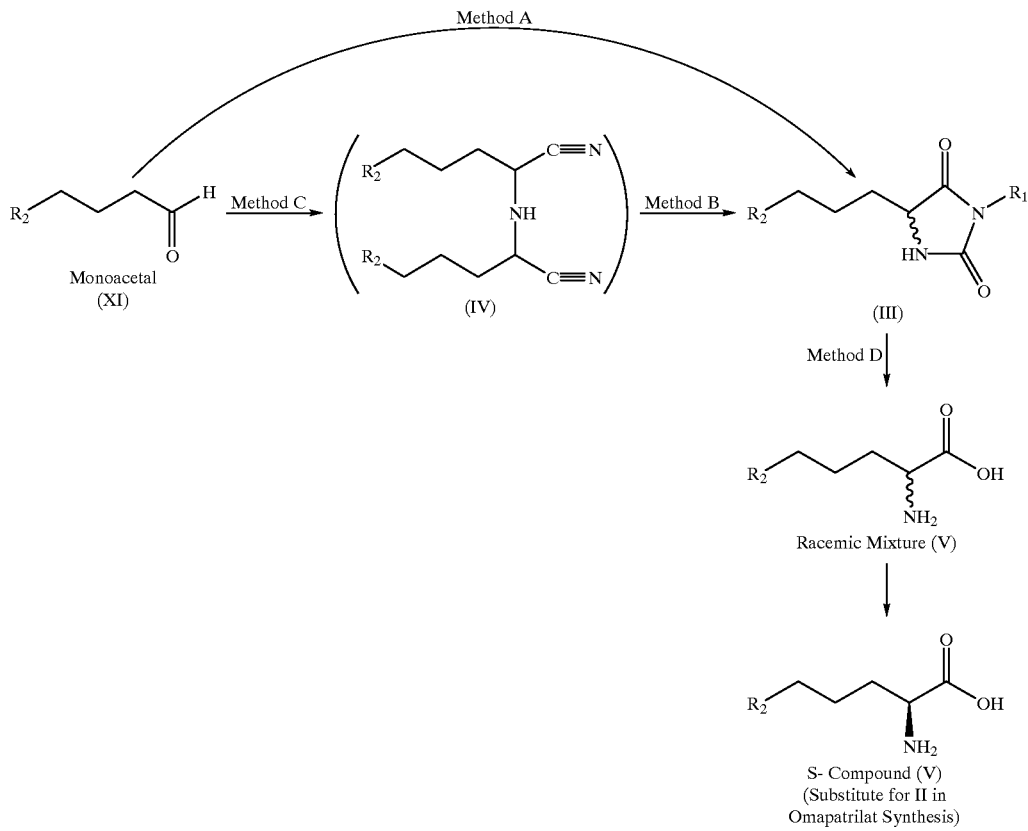

wherein $R_1$ is —H, a $C_1$–$C_5$ alkyl group or a benzyl group and each $R_2$ is as defined above.

As set forth in this reaction pathway, compound (IV) may be an intermediate in the synthesis of hydantoin (III). Hydantoin (III) is used as an intermediate in the synthesis of racemic mixture (V).

The S-stereoisomer of racemic mixture (V) may be used in place of compound (II) in the synthesis of omapatrilat (I).

The use of the S-stereoisomer of racemic mixture (V) with its protected aldehyde avoids the need to oxidize the alcohol on compound (II) and thus reduces the number of steps necessary for the synthesis of omapatrilat and farther avoids the use of noxious chemicals. See Robl, J. A., et al. *J. Med. Chem.* 1997, 40, 1570–1577; Robl, J. A., et al. *J. Med. Chem.* 1996, 39, 494–502.

Referring to the overall reaction scheme above, hydantoin (III) may be synthesized by one of the two reactions:

(METHOD A)

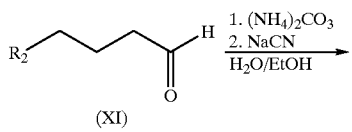

-continued

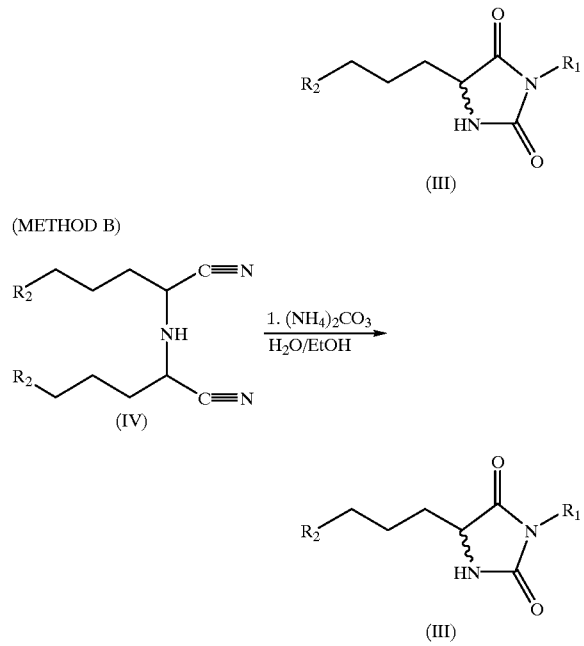

Compound (IV) may be synthesized by the following reaction:

(METHOD C)

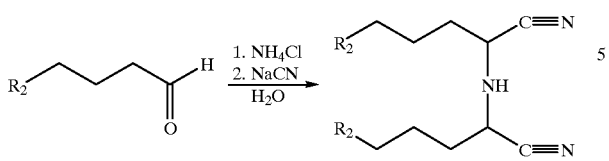

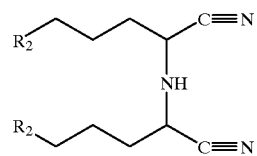

wherein each $R_2$ is independently selected from:

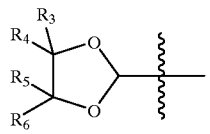 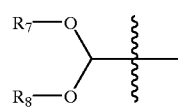

Racemic mixture (V) may be synthesized by the following reaction:

(METHOD D)

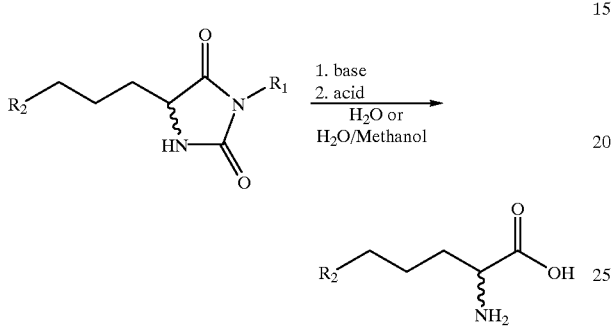

and further wherein $R_3$, $R_4$, $R_5$, and R6 are independently selected from the group consisting of —H or a $C_1$–$C_5$ alkyl group. (In a preferred embodiment $R_3$, $R_4$, $R_5$, and $R_6$ are independently selected from a group consisting of —H or a $C_1$–$C_3$ alkyl group. In a more preferred embodiment $R_3$, $R_4$, $R_5$, and R6 are independently selected from the group consisting of a $C_1$–$C_3$ alkyl group; or $R_3$, $R_4$, $R_5$, and R6 are all —H); and $R_7$ and $R_8$ are independently selected from the group consisting of a $C_1$–$C_5$ alkyl group. In a preferred embodiment $R_7$ and $R_8$ are independently selected from a group consisting of a $C_1$–$C_3$ alkyl group.

DETAILED DESCRIPTION OF THE PREFERRED EMBODIMENTS

The invention is directed to the intermediate (IV) containing two nitrile groups:

The inventive process relating to the production of the dinitrile of formula (IV) from the monoacetal of formula (XI) will be referred to herein as "Method C." "Method C" is part of the overall reaction scheme:

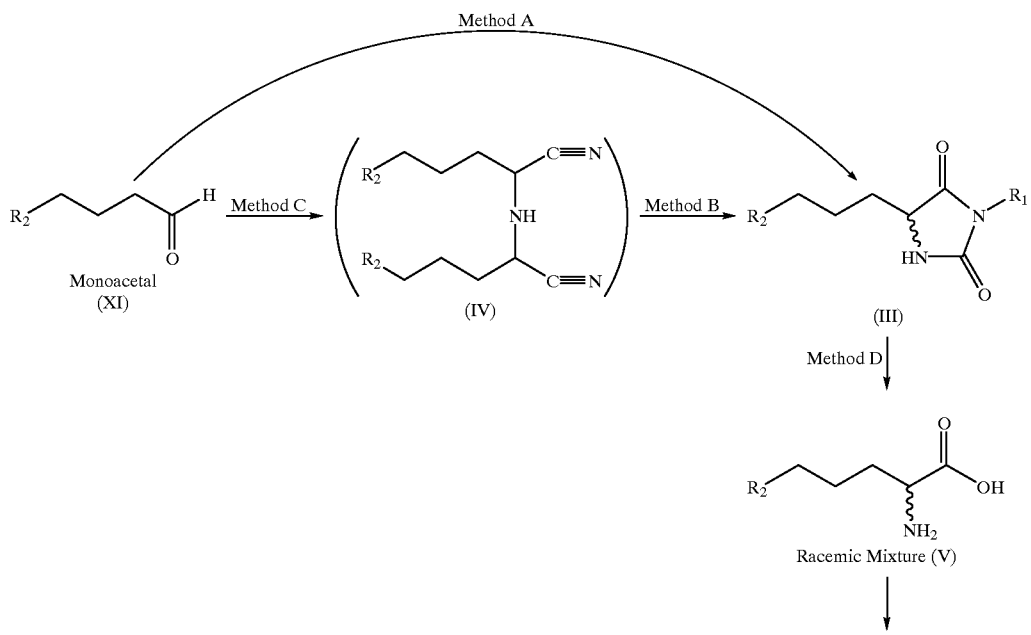

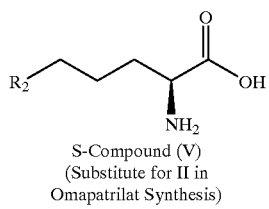

S-Compound (V)
(Substitute for II in
Omapatrilat Synthesis)

The production of the hydantoin of formula (III) from the dinitrile will be referred to herein as "Method B." The hydantoin can alternatively be produced directly from the monoacetal of formula (XI). This reaction will be referred to as "Method A." The production of the racemic mixture of formula (V) from the hydantoin will be referred to as "Method D."

The dinitrile compound of the invention is used to produce the hydantoin of the formula:

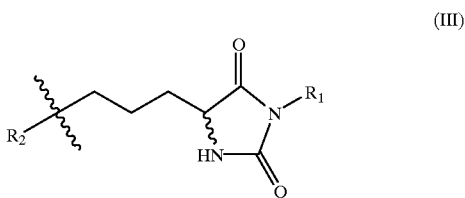

(III)

wherein $R_1$ is —H, a $C_1$–$C_5$ alkyl group or a benzyl group and $R_2$ is as described above. In a preferred embodiment, $R_1$ is —H or a $C_1$–$C_3$ alkyl group.

Compound (III) is used as an intermediate in the synthesis of racemic mixture (V):

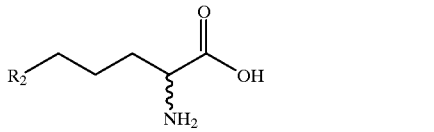

(V)

wherein $R_2$ is as defined above.

The S stereoisomer of compound (V) may be obtained by subjecting the racemic mixture of formula (V) to amidation in water. A molar excess (generally 10 to 20 percent excess) of acetic anhydride is typically used to ensure complete acylation of all of the nitrogen groups on the compound of formula (V). The reaction is conducted at approximately 35° C. The amide linkage on the desired S-isomer may then be cleaved by enzymatic activity, thereby leaving the undesired R isomer in solution. The free amino acid is then collected and purified. The S-stereoisomer of compound (V) may be purified in the same manner as the (S)-hydroxy amino acid compound (II) with a theoretical yield of 50%. (See Robl, J. A., et al. *J. Med. Chem.* 1997, 40, 1570–1577). The purified isomer may then be used to substitute for compound (II) as a synthetic starting material for generating omapatrilat.

An advantage in using compound (V) with its protected aldehyde is that it avoids the need to oxidize the alcohol on compound (II) and thus reduces the number of steps necessary for the synthesis of omapatrilat. It further avoids the use of noxious chemicals often employed in the oxidation of compound (II). See Robl, J. A., et al. *J. Med. Chem.* 1997, 40, 1570–1577; Robl, J. A., et al. *J. Med. Chem.* 1996, 39, 494–502.

An additional advantage in using compound (III) in the synthesis is the high efficiency evidenced when converting compound (III) to the S stereoisomer of compound (V). Hydantoins, such as compound (III), can be enzymatically racemized so that resolved R stereoisomer can be converted to and purified as the S stereoisomer, thereby increasing the possible yields of the desired S stereoisomer.

Compound (III) may be synthesized by either Method A or Method B. Method A is summarized below:

(METHOD A)

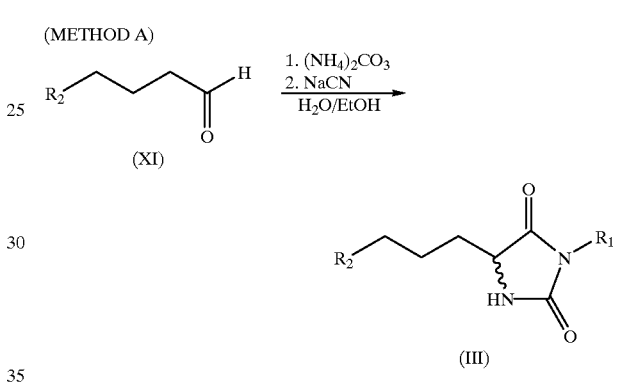

Any alkali cyanide, such as LiCN, as well as any organic cyanohydrin, such as a $C_1$–$C_6$ aliphatic cyanohydrin, may be used in place of NaCN in Method A. The reaction scheme for Method A presented above illustrates the use of a $H_2O$/EtOH blend as reaction medium, though a pure aqueous reaction medium may be used. The alcohol, which may be either methanol, ethanol, isopropyl alcohol, propyl alcohol, butyl alcohol or i-butyl alcohol, increases the solubility of the monoacetal of formula (I) in water. Typically, the weight ratio of water:$C_1$–$C_4$ alcohol in the reaction medium is 1:1 or more. The weight ratio of monoacetal::cyanide compound is typically between 2:1. The weight ratio of cyanide:ammonium carbonate is generally 1:13; and the weight ratio of reaction medium:monoacetal is typically 28:1.

In a preferred embodiment, the reaction mixture is heated above room temperature, (20° C.). In a more preferred embodiment, the reaction mixture is heated to about 50° C. to about 57° C. The reaction mixture is allowed to react for a time sufficient to effectuate the reaction, preferably more than 2 hrs and more preferably greater than 6 hrs and even more preferably greater than 12 hours. In a preferred embodiment, the reaction product is recovered by adjusting the system pH from about 6 to about 10, preferably about 7, at which time the reaction product forms a solid white powder. The reaction is conducted at ambient pressure. Method (A) may further generate a minor amount of compound (IV) as an intermediate chemical species.

The dinitrile compound of the invention, formula (IV), is principally produced when the source of ammonium ion, i.e., ammonium carbonate in Method A, is replaced with another inorganic or an organic ammonium salt. The synthesis denoted as Method C may be schematically represented as:

(METHOD C)

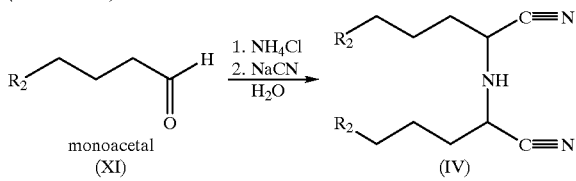

Suitable for use as the ammonium compound for Method C is ammonium chloride or any other inorganic ammonium compound, such as ammonium sulfate, or an organic containing ammonium compound. The cyano compound used in Method A may likewise be used in Method C. The weight ratio of ammonium compound:cyanide containing compound for Method C is generally about 1:1. In addition, the aqueous media in Method C may be substituted with a $C_1$–$C_4$ alkanol as discussed above for Method A. The weight ratio of reaction medium to monoacetal is about 4:1 and the weight ratio of cyanide containing compound:reaction medium is about 1:12.5.

In a preferred embodiment the reaction mixture for Method C is heated above room temperature (20° C.), preferably from 50° C. to about 52° C. at ambient temperature. The reaction mixture is allowed to react for an adequate amount of time to produce the compound of formula (IV), preferably more than 10 minutes, more preferably greater than 1 hour, and most preferably 2 hours or more. The pH of the reaction mixture is typically maintained between about 6 to about 10. In a preferred embodiment, the product is recovered from the organic phase by crystallization from acetone/water, more preferably followed by washing with toluene.

The dinitrile compound of formula (IV) may be converted to compound (III) as shown in Method (B):

(METHOD B)

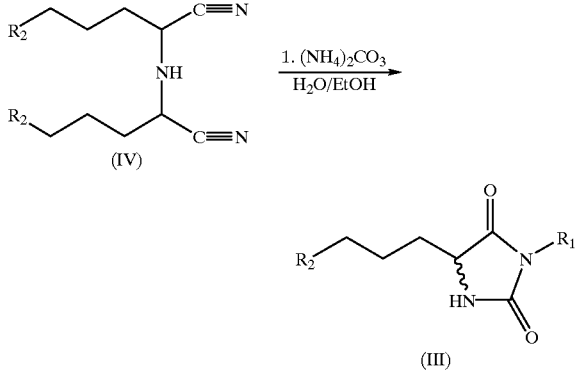

Thus, the use of a non-carbonate inorganic ammonium salt, such as ammonium chloride, or an organo ammonium containing compound (versus ammonium carbonate), causes the formation of the dinitrile compound (IV). Conversion of the dinitrile compound (IV) to the hydantoin (III) requires the additional step of reacting the intermediate compound (IV) with carbon dioxide or a carbon dioxide generating compound such as ammonium carbonate. In a preferred embodiment, the addition of an alkali or ammonium hydroxide is also used in order to assist in the formation of the carbon dioxide. The weight ratio of carbon dioxide or carbon dioxide generating compound:hydroxide is generally between 1:1.75 and the weight ratio of carbon dioxide or carbon dioxide generating compound:reaction medium is generally 1:7.5.

In place of the $H_2O$/EtOH mixture, the reaction media can be purely water or any a mixture of any of the $C_1$–$C_4$ alcohols referenced above. The reaction mixture in Method B is allowed to proceed generally at room temperature and at ambient or above atmospheric pressure (up to about 60 psig) for 10 minutes or more, more preferably for 2 hours or more and even more preferably for at least 6 hours at a pH of between from about 6 to about 10. In a preferred embodiment, the solution is brought to a pH of 7.5.

Compound (V) is produced from the hydantoin as summarized in Method D:

(METHOD D)

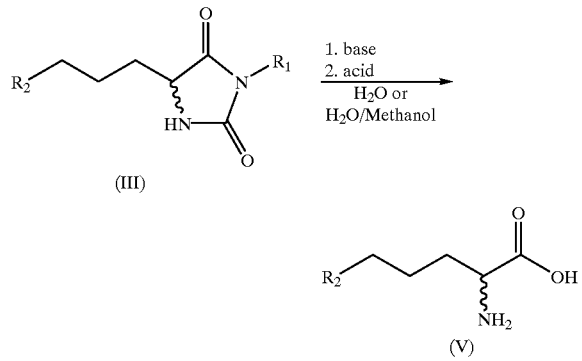

The base in the reaction mixture of Method D is an alkali hydroxide, preferably either sodium hydroxide or lithium hydroxide, and the acid is preferably acetic acid, dilute hydrochloric acid or sulfuric acid, most preferably acetic acid. The weight ratio of hydantoin to alkali hydroxide to reaction media is about 1:1:6. In a preferred embodiment the reaction mixture (D) is heated above room temperature (20° C.) and in a more preferred embodiment is heated to 100° C. or higher, and in an even more preferred embodiment is heated to 150° C. The reaction mixture is allowed to react for an adequate amount of time to produce the desired racemic mixture. This adequate reaction time is preferably more than 10 minutes and more preferably greater than 1 hour and even more preferably greater than 2 hours. During the reaction, the pH increases to about 12 or higher. The reaction mixture (D) is brought to pH 7 with the acid. The weight ratio of base:acid in the reaction is generally about 1:1.4.

The following examples will illustrate the practice of the present invention in its preferred embodiments. Other embodiments within the scope of the claims herein will be apparent to one skilled in the art from consideration of the specification and practice of the invention as disclosed herein. It is intended that the specification, together with the examples, be considered exemplary only, with the scope and spirit of the invention being indicated by the claims which follow.

EXAMPLE 1

Synthesis of Representative Species of Compound (IV) Wherein $R_2$ is Formula (VIII)

Water (30 g), glutaric dialdehyde monoethylene glycol acetal (monoacetal, 15.1 g) and ammonium chloride (5.58 g) were added together in a 100 mL round bottom flask (mixing by magnetic stirrer). Next sodium cyanide (4.80 g in 20.9 g water) was added. A 16° C. temperature rise was noted. The reaction mixture was heated to 50–52° C. and held at this temperature for 2 hours. The lower organic phase was separated from the upper aqueous phase. The aqueous phase was twice washed with methylene chloride. After solvent removal, the oil was crystallized from acetone/water. After washing with toluene, the white solid was dried.

$^1$H NMR data (300 MHz, $(CD_3)_2SO$): $\delta$1.5–1.9 (m, 12H), 3.76 (m, 1H), 3.8–4.0 (m, 10H), 4.8 (m, 2H). $^{13}$C NMR data (75 MHz, $(CD_3)_2SO$): $\delta$19.6, 32.5, 33.2, 48.1 64.2, 103.4, 120.0. Mass Spectroscopy data (+CI) m/z (relative intensity): 297 ($M^+$–HCN, 21), 270 ($M^+$–2 HCN, 27), 235 ($M^+$–HCN,$CH_2CH_2O$, $H_2O$, 25), 208 ($M^+$–2 HCN, $CH_2CH_2O$, $H_2O$, 100). Anal. Calcd for $C_{16}H_{25}N_3O_4$: C, 59.43; H, 7.79; N, 12.99. Found: C, 59.48; H, 7.92; N, 12.87.

End product $C_{16}H_{25}N_3O_4$, Compound (IX), is represented by the formula:

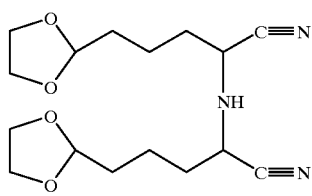

(IX)

EXAMPLE 2

Synthesis of Representative Species of Compound (IV) wherein $R_2$ is formula (VII)

The procedure set forth in Example 1 is repeated. In place of glutaric dialdehyde monoethylene glycol acetal, about 15 g of glutaric dialdehyde dimethanol acetal is used. All other reaction conditions may remain the same.

EXAMPLE 3

Synthesis Representative Species of Compound (III) Wherein $R_2$ is Formula (VIII)

Water (190 g) was added to a 2 liter round bottom flask (mechanically stirred). Next, ammonium carbonate (174.9 g) was added to the water. More water (195 g) and ethanol (385 g) were added to the flask, followed by sodium cyanide (13.3 g). Glutaric dialdehyde monoethylene glycol acetal (monoacetal, 30.0 g) was added in one portion. A 7° C. temperature rise was noted. The reaction mixture was heated to 50–57° C. and held at this temperature for 12.3 hours. The reaction volume was reduced (490.8 g taken as overhead). System pH was brought to 7 with 25% $H_2SO_4$ at which time a solid white powder formed in the flask. The solid was recrystallized from water and dried.

End product, compound (X), is represented by the formula:

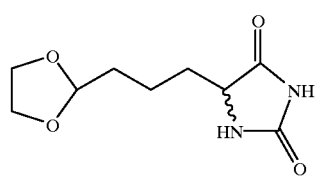

(X)

EXAMPLE 4

Synthesis Representative Species of Compound (III) Wherein $R_2$ is formula (VII)

The procedure set forth in Example 3 is repeated. In place of glutaric dialdehyde monoethylene glycol acetal, about 30 g of glutaric dialdehyde monomethanol acetal is used. All other reaction conditions may remain the same.

EXAMPLE 5

Second Synthesis Scheme for Representative Species of Compound (III)

Water (30 g), glutaric dialdehyde monoethylene glycol acetal (monoacetal, 15.1 g) and ammonium chloride (5.58 g) were added together in a 100 mL round bottom flask (on a magnetic stirrer). Next, sodium cyanide (4.80 g in 20.9 g water) was added over 10 minutes. The reaction was heated to 50–52° C. and held at this temperature for 2 hours. Both phases were transferred to a pressure vessel. The system was heated to 100° C. and carbon dioxide was fed to the reactor. Maximum system pressure was 60 psig. After 6 hours, the solution was cooled and brought to pH 7.5 with acetic acid. The hydantoin was recovered as a white solid.

EXAMPLE 6

Synthesis of Racemic Mixture of Formula (V)

Ammonium chloride (90.8 g, 1.70 moles) in water (1000 g) was cooled to 0–5 C. Next, monoacetal (246 g. 1.17% dialdehyde, 3.56% bisacetal, 1.63 moles) was added to the ammonium chloride solution. While maintaining the system temperature between 0–10 C sodium cyanide (79.3 g, 1.62 moles; in 313.4 g water and 3.9 g 50% NaOH aq. Soln., CAUTION: toxic, exotherm) was added below the surface of the monoacetal solution. Upon completion of the addition the solution was heated to 50° C. for six hours. The solution was cooled to 30° C. Ammonium hydroxide (211 g, 2.22 equivalents; 28–30% in water) was charged and the solution was reheated to 100° C. Gaseous carbon dioxide (133.2 g, slight exotherm) was fed to the reactor at such a rate as to maintain system pressure near 60–65 psig and the reaction temperature at 100° C. The system was held at 100° C. for four hours. Excess carbon dioxide was vented from the system. A portion of the water was boiled overhead to facilitate the removal of ammonia and to make room for the next step. Lithium hydroxide (226.4 g, 3.33 equivalents; 10% in water) was added after the water strip. The system was brought to 150° C. for four hours. The reaction system was then cooled, filtered (235.2 g wet cake) and neutralized with acetic acid (310 g) to a pH of 7.2–7.4. After a water strip (1878.3 g overhead) methanol (2400 g) was added to precipitate the racemic amino acid. The white solid was washed with cold methanol after recovery. A racemic mixture of formula (V) wherein $R_2$ is (VIII) was obtained.

What is claimed is:

1. A compound of the formula:

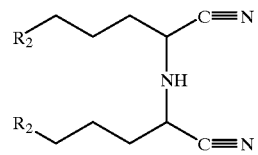

wherein each $R_2$ is independently represented by the formula:

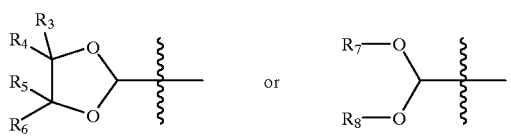

wherein $R_3$, $R_4$, $R_5$, and $R_6$ are independently selected from the group consisting of —H or a $C_1$–$C_5$ alkyl group and $R_7$ and $R_8$ are independently selected from the group consisting of a $C_1$–$C_5$ alkyl group.

2. The compound of claim 1, wherein at least one $R_2$ is of the formula:

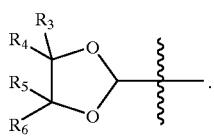

3. The compound of claim 2, wherein $R_3$, $R_4$, $R_5$, and $R_6$ are independently selected from the group consisting of —H or a $C_1$–$C_3$ alkyl group.

4. The compound of claim 3, wherein $R_3$, $R_4$, $R_5$, and $R_6$ are all hydrogen.

5. The compound of claim 1, wherein $R_3$, $R_4$, $R_5$, and $R_6$ are all hydrogen.

6. The compound of claim 1, wherein at least one $R_2$ is

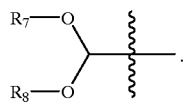

7. The compound of claim 6, wherein $R_7$ and $R_8$ are independently selected from the group consisting of a $C_1$–$C_3$ alkyl group.

8. The compound of claim 1, wherein both $R_2$ are:

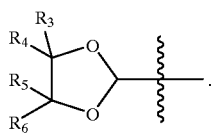

9. The compound of claim 8, wherein $R_3$, $R_4$, $R_5$ and $R_6$ are independently selected from —H or a $C_1$–$C_3$ alkyl group.

10. The compound of claim 8, wherein $R_3$, $R_4$, $R_5$, and $R_6$ on each $R_2$ are —H.

11. The compound of claim 6, wherein both $R_2$ are of the formula:

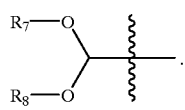

12. A compound of the formula:

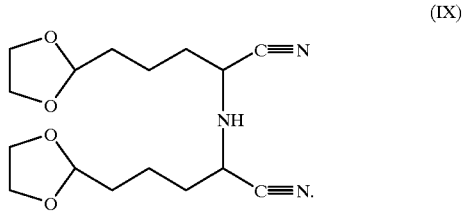

(IX)

13. A process of preparing a compound of the formula:

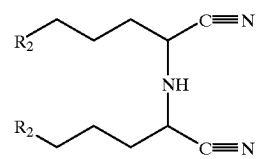

(IV)

wherein each $R_2$ is independently selected from

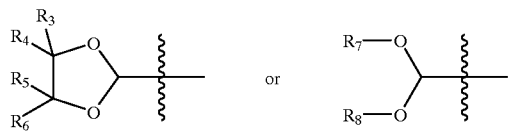

and further wherein $R_3$, $R_4$, $R_5$, and $R_6$ are independently selected from the group consisting of —H or a $C_1$–$C_5$ alkyl group and $R_7$ and $R_8$ are independently selected from the group consisting of a $C_1$–$C_5$ alkyl group, said process comprising mixing in an aqueous medium a monoacetal having the formula:

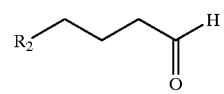

with a non-carbonate ammonium salt and an alkali cyanide for a time and at a temperature sufficient to generate the compound of formula (IV).

14. The process of claim 13, wherein the alkali cyanide is NaCN or LiCN.

15. The process of claim 13, wherein the non-carbonate ammonium salt is ammonium chloride.

16. The process of claim 13, wherein the mixture is maintained at a temperature between from about 50° to about 52° C.

17. The process of claim 13, wherein $R_3$, $R_4$, $R_5$ and $R_6$ are independently selected from the group consisting of a $C_1$–$C_3$ alkyl group.

18. The process of claim 13, wherein the weight ratio of non-carbonate ammonium salt to alkali cyanide is about 1:1.

19. The process of claim 13, wherein the aqueous medium further contains a $C_1$–$C_4$ alkanol.

20. A compound of the formula:

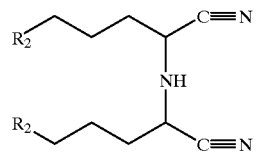

(IV)

wherein each $R_2$ is independently selected from:

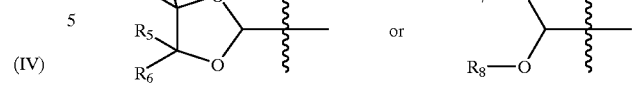

and further wherein $R_3$, $R_4$, $R_5$, and $R_6$ are independently selected from the group consisting of —H or a $C_1$–$C_5$ alkyl group and $R_7$ and $R_8$ are independently selected from the group consisting of a $C_1$–$C_5$ alkyl group; produced by the process of claim 13.

* * * * *